(12) United States Patent
Engel et al.

(10) Patent No.: US 8,551,977 B2
(45) Date of Patent: *Oct. 8, 2013

(54) USE OF PERIFOSINE IN COMBINATION WITH ANTIMETABOLITES FOR THE TREATMENT OF BENIGN AND MALIGNANT ONCOSES IN HUMANS AND MAMMALS

(75) Inventors: Jurgen Engel, Alzenau (DE); Eckhard Gunther, Maintal (DE); Herbert Sindermann, Rodgau (DE)

(73) Assignee: AEterna Zentaris GmbH, Frankfurt (DE)

( * ) Notice: Subject to any disclaimer, the term of this patent is extended or adjusted under 35 U.S.C. 154(b) by 185 days.

This patent is subject to a terminal disclaimer.

(21) Appl. No.: 12/751,454

(22) Filed: Mar. 31, 2010

(65) Prior Publication Data

US 2010/0190738 A1    Jul. 29, 2010

Related U.S. Application Data

(63) Continuation of application No. 10/632,187, filed on Jul. 30, 2003, now Pat. No. 8,389,497.

(60) Provisional application No. 60/399,615, filed on Jul. 30, 2002.

(51) Int. Cl.
  *A61K 31/70*  (2006.01)
  *A61K 31/685*  (2006.01)

(52) U.S. Cl.
  USPC ............................................................ 514/77

(58) Field of Classification Search
  USPC ................................................... 514/49, 77
  See application file for complete search history.

(56) References Cited

U.S. PATENT DOCUMENTS

| | | | |
|---|---|---|---|
| 5,219,866 A | 6/1993 | Schumacher et al. | |
| 5,942,639 A | 8/1999 | Engel et al. | |
| 6,093,704 A | 7/2000 | Nickel et al. | |
| 6,172,050 B1 * | 1/2001 | Nossner et al. | 514/79 |
| 6,583,127 B1 | 6/2003 | Gajate et al. | |
| 6,696,428 B2 | 2/2004 | Nickel et al. | |
| 6,800,639 B2 * | 10/2004 | Giles et al. | 514/300 |
| 6,903,080 B2 | 6/2005 | Nossner et al. | |
| 2007/0167408 A1 | 7/2007 | Perrissoud et al. | |
| 2011/0243933 A1 | 10/2011 | Poradosu et al. | |

FOREIGN PATENT DOCUMENTS

| EP | 1 545 553 B1 | | 7/2011 |
|---|---|---|---|
| WO | WO 99/37289 | * | 7/1999 |
| WO | WO 00/33917 | | 6/2000 |
| WO | WO 02/066019 A2 | | 8/2002 |
| WO | WO 03/005522 A1 | | 7/2003 |
| WO | WO 2004012744 | | 2/2004 |
| WO | WO 2005/000318 | | 1/2005 |
| WO | WO 2006/081452 | | 8/2006 |
| WO | WO 2011/123691 A1 | | 10/2011 |

OTHER PUBLICATIONS

Manfred E. Wolff, Burger's Medicinal Chemistry and Drug Discovery, 5th edition, vol. 1, 1995, pp. 975-997.*
Goodman and Gilman The pharmacological basis of therapeutic 9th Edition (1996) 1225-32.*
Banker (Modem Pharmaceutics) Banker, G.S. et al, "Modem Pharmaceutics, 3ed.",Marcel Dekker, NewYork, 1996, pp. 451 and 596.*
Awada et al. European J. of Cancer (2002) 38773-778.*
Hilgard et al (Advances in Exp. Med. And Biol, US (1996)157-164 (XP 00225712).*
Georgieva et al. Cancer Letters 182(2) 163-174 (2002).*
Dictionary2.com (2000) 1 page.*
ASCO Abstract 2006—Journal of Clinical Oncology, 2006 ASCO Annual Meeting Proceedings (Post-Meeting Edition)m vol. 24, No. 18S (June 20 Supplement), 2006.
ASCO Abstract 2009—Journal of Clinical Oncology, 2009 ASCO Annual Meeting Proceedings (Post-Meeting Edition)m vol. 27, No. 15S (May 20 Supplement), 2009:4081.
Ayala, Gustavo, et al., Bortezomib-Mediated Inhibition of Steroid Receptor Coactivator-3 Degradation Leads to Activated Akt, Clin Cancer Res, Nov. 15, 2008, 7511-7518, 14(22).
Catley Laurence, et al., Alkyl Phospholipid Perifosine Induces Myeloid Hyperplasia in a Murine Myeloma Model, Experimental Hematology, 35 (2007), 1038-1046.
Chiarini, F., et al., The novel Akt Inhibitor, Perifosine, Induces Caspase-Dependent Apoptosis and Downregulates P-glycoprotein Expression in Multidrug-Resistant Human T-acute Leukemia Cells by a JNK-dependent Mechanism, Leukemia (2008) 22, 1106-1116.
Cirstea, Diana, et al., Dual Inhibition of Akt/Mammalian Target of Rapamycin Pathway by Nanoparticle Albumin-Bound-Rapamycin and Perifosine Induces Antitumor Activity in Multiple Myeloma, Mol Cancer Ther, Apr. 2010, 963-975, 9(4).
Crul, M., et al. Phase I and Pharmacological Study of Daily Oral Administration of Perifosine (D-21266) in Patients with Advanced Solid Tumours, European Journal of Cancer, 38 (2002), 1615-1621.
Dasmahapatra Girija P., et al., In vitro Combination Treatment with Perfosine and UCN-01 Demonstrates Synergism Against Prostate (PC-3) and Lung (A549) Eptithelial Adenocarcinoma Cell Lines, Clin Cancer Res, Aug. 1, 2004, 5242-5252, vol. 10.

(Continued)

*Primary Examiner* — Shirley V Gembeh
(74) *Attorney, Agent, or Firm* — Goodwin Procter LLP

(57) ABSTRACT

The invention relates to the use of alkylphosphocholines in combination with antimetabolite antitumor substances for the treatment of benign and malignant oncoses in humans and animals. It is possible in this connection for the alkylphosphocholines to be employed in a combination according to the invention with one or more antimetabolite antitumor substances. Preferred alkylphosphocholines are described by the Formula II.

Formula II

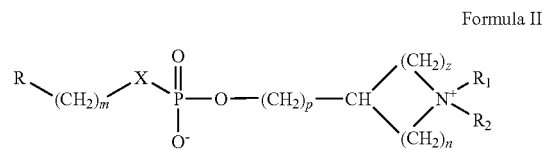

One such preferred alkylphosphocholine is perifosine.

19 Claims, No Drawings

(56) References Cited

OTHER PUBLICATIONS

David, E., et al., Perifosine Synergistically Enhances TRAIL-Induced Myeloma Cell Apoptosis via Up-Regulation of Death Receptors, Clin Cancer Res 2008:14(16) Aug. 15, 2008, 5090-5098.

Dogan, S. Serdar, Ocular Side Effects Associated with Imatinib Mesylate and Perifosine for Gastrointestinal Stromal Tumor, Hematol Oncol. Clin N Am, 23 (2009) 109-114.

Ellis, Matthew J., et al., "PIKing" the Winner for Phospatidylinositol 3-Kinase Inhibitors in ErbB2-Positive Breast Cancer: Let's Not "PTENed" It's Easy!, Clin Cancer Res, Oct. 1, 2007, 5661-5662, 13(19).

Engel, Jörg B., et al., Induction of Programmed Cell Death by Inhibition of AKT with the Alkylphosphochloine Perifosine in In Vitro Models of Platinum Sensitive and Resistant Ovarian Cancers, Arch Gynecol Obstet, doi:10.1007/s00404-010-1457-6; published online Apr. 20, 2010.

Engel, Jörg B., et al., Perifone Inhibits Growth of Human Experimental Endometrial Cancers by Blockade of AKT Phosphorylation, Eur J. Obstet. Gynecol (2008), doi:10.1016/j.ejogrb.2008.06.007.

Ernst, D. Scott, et al. Phase II Study of Perifosine in Previously Untreated Patients with Metastatic Melanoma, Investiational New Drugs, 23:569-576, 2005.

Festuccia, Claudio, et al., Akt Down-Modulation Induces Apoptosis of Human Prostate Cancer Cells and Synergizes with EGFR Tyrosine Kinase Inhibitors, The Prostate, 58:965-974 (2008).

Floryk, Daniel, et al., Perifosine Induces Differentiation and Cell Death in Prostate Cancer Cells, Cancer Letters, 266 (2008) 216-226.

Fomchenko, Elena I., et al., Mouse Models of Brain Tumors and Their Applications in Preclinical Trials, Clin Cancer Res., 2006:12(18) Sep. 15, 2006; 5288-5297.

Fu, Lei, et al., Perifosine Inhibits Mammalian Target of Rapamycin Signaling through Facilitating Degradation of Major Components in the mTOR Axis and Induces Autophagy, Cancer Res, Dec. 1, 2009, 8967-8976, 69(23).

Gajate, Consuelo, et al., Edelfosine and Perifosine Induce Selective Apoptosis in Multiple Myeloma by Recruitment of Death Receptors and Downstream Signaling Molecules into Lipids Rafts, Blood, Jan. 15, 2007, 711-719, vol. 109, No. 2.

Harvey, R. Donald, et al., P13 Kinase/AKT Pathway as a Therapeutic Target in Multiple Myeloma, Future Oncol., (2007) 3(6), 639-647.

Hideshima, Teru, et al., Perifosine, An Oral Bioactive Novel Alkylphospholipid, Inhibits Akt and Induces in Vitro and In Vivo Cytotoxicity in Human Multiple Myeloma Cells, Blood First Edition Paper, Jan. 17, 2006, 1-34, doi 10.1182/blood-2005-08-3434.

Hideshima, Teru, et al., Inhibition of Akt Induces Significant Downregulation of Survivin and Cytotoxicity in Human Multiple Myeloma Cells, British Journal of Haematology, 2007, 138, 783-791.

Huston, Alissa, et al., Targeting and Heat Shock Protein 90 Produces Synergistic Multiple Myeloma Cell Cytotoxicity in the Bone Marrow Microenvironment, Clin Cancer Res, Feb. 1, 2008, 865-874, 14(3).

Jendrossek, V., et al., Membrane Targeted Anticancer Drugs: Potent Inducers of Apoptosis and Putative Radiosensitisers, Curr. Med. Chem.—Anti-Cancer Agents, 2003, 3, 343-353.

Knowling, M., et al., A Phase II Study of Perifosine (D-21226) in Patients with Previously Untreated Metastatic or Locally Advanced Soft Tissue Sacoma: A National Cancer Institue of Canada Clinical Trials Group Trial, Invest New Drugs, (2006), 24:435-439.

Kodach, Liudmila L., vilacein Synergistically Increases 5-fluorouracil Cytotoxicity, Induces Apoptosis and Inhibits Akt-mediated Signal Transduciton in Human Colorectal Cancer Cells, Carcinogenesis, 2006, vol. 27, No. 3, 508-516.

Konstantinov, Spiro M., et al., BCR-ABL Influcences the Antileukaemic Efficacy of Alkylphosphocholines, British Journal of Haematology, 1999, 107, 365-374.

Konstantinov, Spiro M., et al., Human Urinary Bladder Carcinoma Cell Lines Respond to Treatment with Alkylphosphocholines, Cancer Letters, 1999, 144, 153-160.

Konstantinov, Spiro M., et al., Alkylphosphocholines: Effects on Human Leukemic Cell Lines and Normal Bone Marrow Cells, Int. J. Cancer, 1998, 77, 778-786.

Kumar, Anil, et al., The Alkylphospholipid Perifosine Induces Apoptosis and p21-Mediated Cell Cycle Arrest in Medulloblastoma, Mol Cancer Res, Nov. 2009, 1813-1821, 7(11).

Leighl, Natasha B., et al., A Phase 2 Study of Perifosine in Advanced or Metastatic Breast Cancer, Breast Cancer Res Treat (2008), 108:87-92.

Leleu, Xavier, et al., Targeting NF-κB in Waldenstrom Macroglobulinemia, Blood, May 15, 2008, 111(10), 5068-5077.

Li, X., et al., Enhancement of Antitumor Activity of the Anti-EGF Receptor Monoclonal Antibody Cetuximab/C225 by Perifosine in PTEN-deficient Cancer Cells, Onocogen, (2005), 1-11.

Lopiccolo, Jaclyn, et al., Targeting the P13K/Akt/mTOR Pathway: Effective Combinations and Clinical Considerations, Drug Resistance Updates, 11 (2008) 32-50.

Mitsiades, Constantin S., et al., Emerging Treatments for Multiple Myeloma: Beyond Immunomodulatory Drugs and Bortezomib, Seminars in Hematology, Apr. 2009, vol. 46, No. 2, 166-175.

Momota, Hiroyuki, et al., Perifosine Inhibits Multiple Signaling Pathways in Glial Progenitors and Cooperates With Temozolomide to Arrest Cell Proliferation in Gliomas In Vivo, Cancer Res, Aug. 15, 2005, 65(16), 7429-7435.

Nelson, EC, et al., Inhibition of Akt Pathways in the Treatment of Prostate Cancer, Prostate Cancer and Prostatic Diseases, (2007), 10, 331-339.

Nyåkern, Maria, et al., Synergistic Induction of Apoptosis in Human Leukemia T Cells by the Akt Inhibitor Perifosine and Etoposide Through Activation of Intrinsic and Fas-mediated Extrinsic Cell Death Pathways, Mol Cancer Ther, Jun. 2006, 5(6), 1559-1570.

Papa, V., et al., Proapoptotic Activity and Chemosensitizing Effect of the Novel Akt Inhibitor Perifosine in Acute Myelogenous Leukemia Cells, Leukemia, (2008), 22, 147-160.

Patel, Vyomesh, Perifosine, A Novel Alkylphospholipid, Induces p21WAF1 Expression in Squamous Carcinoma Cells Through a P53-independent Pathway, Leading to Loss in Cyclin-dependent Kinase Activity and Cell Cycle Arrest, Cancer Research, 62, 1401-1409, 2002.

Porta, Camillo, et al., Phosphatidylinositol-3-Kinase/Akt Signaling Pathway and Kidney Cancer, and the therapeutic Potential of Phosphatidylinositol-3-Kinase/Akt Inhibitors, The Journal of Urology, Dec. 2009, vol. 182, 2569-2577.

Rahmani, Mohamed, et al., Coadmininstration of Histone Deacetylase Inhibitors and Perifosine Synergistically Induces Apoptosis in Human Leukemia Cells Through Akt and ERK1/2 Inactivation and the Generation of Ceramide and Reactive Oxygen Species, Cancer Res, 2005, 2422-2432.

Tazaari, Pier Luigi, et al., Synergistic Proapoptotic Activity of Recombinant TRAIL Plus the Akt Inhibitor Perifosone in Acute Myelogenous Leukemia Cells, Cancer Res, Nov. 15, 2008, 68 (22), 9394-9403.

Ummersen et al., A Phase I Trial of Perifosine (NSC 639966) on a Loading Dose/Maintenance Dose Schedule in Patients with Advanced Cancer, Clinical Cancer Research, vol. 10, 7450-7456, Nov. 15, 2004.

Unger, Clemens, et al., First-Time-In-Man and Pharmacokinetic Study of Weekly Oral Perifosine in Patients with Solid Tumours, European Journal of Cancer, 46 (2010), 920-925.

Vinall, Ruth L., et al., Combination Treatment of Prostate Cancer Cell Lines with Bioactive Soy Isoflavones and Perifones Causes Increased Growth Arrest and/or Apoptosis, Clin Cancer Res, Oct. 15, 2007, 13(20), 6204-6216.

Vink, Stefan R., et al., Tumor and Normal Tissue Pharmacokinetics of Perifosine, An Oral Anti-Cancer Alkylphospholipid, Investigational New Drugs, 23, 2005, 279-286.

Vink, Stefan R., et al., Phase I and Pharmacokinetic Study of Combined Treatment With Perifosine and Radiation in Patients With Advanced Solid Tumours, Radiotherapy and Oncology, 80, 2006, 207-213.

Voltan, R., et al., Perifosine Plus Nutlin-3 Combination Shows a Synergistic Anti-Leukaemic Activity, British Journal of Haematology, 2010, 148(6), 957-961.

Younes, Hashem, et al., Targeting the Phosphatidylinositol 3-Kinase Pathway in Multiple Myeloma, Clin Cancer Res, Jul. 1, 2007, 13(13), 3771-3775.

Chou, Ting-Chao, Drug Combination Studies and Their Synergy Quantification Using the Chou-Talalay Method, Molecular Pharmacology and Chemistry Program, Memorial Sloan-Kettering Cancer Center, New York, NY USA. Cancer Reseach (2010), 70(2), 440-446.

Chou, Ting-Chao et al., Quantitative analysis of dose-effect relationships: the combined effects of multiple drugs or enyzme inhibitors, Lab. Pharmacol., Mem. Sloan-Kettering Cancer Cent., New York, NY, USA. Advances in Enzyme Regulation (1984), 22 27-55.

Page Brigitte, et al., A new fluorometric assay for cytotoxicity measurements in vitro, International Journal of Oncology 3: 473-476, 1993.

European Search Report dated Sep. 3, 2008.

Principe et al., Synergistic cytotoxic effect of aza-alkylphospholipids in association with chemotherapeutic drugs, J. Lipid Mediators Cell Signalling, 10. 1994, pp. 171-173.

Principe et al., Evaluation of combinations of antineoplastic ether phospholipids and chemotherapeutic drugs, Anti-Cancer Drugs, 3, 1992. pp. 577-587.

Ruiter et al., Alkyl-Lysophospholipids As Anticancer Agents and Enhancers of Radiation-Induced Apoptosis, Int. J, Radiation Oncology aiol. Phys.. 49(2), 2001, pp. 415-419.

Maly et el., Interference of new alkytphospholipid analogues with mitogenic signal transduction, Anti-Cancer Drug Design. 10. 1995. pp. 411-425.

Lohmeyer at al., Antitumor ether lipids and alkylphosphocholines, Drugs of the Future, 19 (11),1994, pp. 1021-1037.

Hilgard et al, D-21266, a New Heterocyclic Alkylphospholipid with Antitumour Activity, European Journal of Cancer, 33(3), 1997, pp. 442-446.

Thilo Sprub, Gunther Bernhardt, Helmut Schoenenberger and Jurgen Engel, Antitumor activity of miltefosine alone and after combination with platinum complexes on MXT mouse mammary carcinoma models; J Cancer Res Clin Oncol (1993) 119:142-149.

P. Hilgard, J. Stekar, T. Klenner, G. Nossner, B. Kutscher, and J. Engel; Heterocyclic Alkylphospholipids With an Improved Therapeutic Range; Advances in Experimental Medicine and Biology, United States (1996),157-164 (XP-002256712).

J. Stekar, P. Hilgard and T. Klenner; Opposite Effect of Miltefosine on the Antineoplastic Activity and Haematological Toxicity of Cyclophosphamide; Eur J Cancer, vol. 31A, No. 3, pp. 372-374,1995 (XP-002256713).

Milka C. Georgieva, Spiro M. Konstantinov, Margarit Topashka-Ancheva, Martin R Berger; Combination effects of alkylphosphocholines and gemcitabine in malignant and normal hematopoietic cells; Cancer Letters 182 (2002) 163-174 (XP-002256714).

D Berkovic, Eam Fleer, J Breass, J Pfortner, E Schleyer and W Hiddenmann; The influence of 1-B-D-arabinofuranosylcytosine on the metabolism of phosphatidylcholine in human leukemic HL 60 and Raji cells; Leukemia (1997) 11, 2079-2086 (XP-002256715).

Shoji M.; Raynor RL.; Fleer E.A.; Eibl H.; Vogler W.R; Kuo J.F.; Effects of hexadecylphosphocholine on protein kinase C and TPA-induced differentiation of HL60 cells; Journal Article (Feb. 1991) vol. 26, No. 2, 145-149 (XP-002256716).

O. Miyazaki, M. Hiratsuka and H. Sugihara, Activation of Caspase 3-Like Protease Is Essential to Octadecyl-(1,1-Dimethyl-4-Piperidino-4-YL)-Phosphate (D-21266)-Induced Apoptosis in Human Squamous Cell Carcinoma KB Cells, Drugs of Today 1998, 34 (Suppl. F): 51-57.

Oliver Rosen, Christiane Schymanietz and Fritz Hölzel, Antiproliferative, cytotoxic and recovery effects in tumor cell cultures treated with synthetic pholpholipids, International Journal of Oncology 5: 517-523, 1994.

Kasianenko et al, topical use of Miltex in patients with Breast Cancer's cutaneous manifestations, 1998:87. (2 pages) Abstract only.

O. Safa, S.M. Parkin and M.C. Bibby, Morphological Changes and Cytokine Gene Expression in Tumor Xenografts Following Treatment With the Alkylphosphocholines Hexadecylphosphocholine and Perifosine, Drugs of Today 1998, 34 (Suppl. F.): 15-26.

Sudhir B. Kondapaka, Sheo S. Singh, Girija P. Dasmahapartra, Edward A. Sausville, and Krishnendu K. Roy, Perifosine, a novel alkylphospholipid, inhibits protein kinase B activation, Molecular Cancer Therapeutics 2003; 2:1093-1103.

Aicher, B. et. al., Perifosine in Combination with Antimetabolites Induces Synergistic Effects on Cytotoxicity and Apoptosis in Human Colon, Multiple Myeloma, Breast, Renal , and Liver Tumor Cell Lines, Abstract #203—22nd EORTC-NCI-AACR Symposium on Molecular Targets and Cancer Therapeutics, Nov. 17, 2010.

Hyo Song Kim et al., Evaluation of anticancer drug sensitivity and gene expression patterns of a novel Akt inhibitor, perifosine in gastric cancer; 2011 AACR Annual Meeting.

Gills, Joell, et al., Perifosine: Update on a Novel Akt Inhibitor, Current Oncology Reports-Evolving Therapies, 2009, 11:102-110.

Kondapaka, Sudhir B., Perifosine, A Novel Alkylphospholipid, Inhibits Protein Kinase B Activation, Molecular Cancer Therapeutics, 2003, 1093-1103.

Australian Search Report dated Oct. 30, 2007.

International Search Report dated Jul. 29, 2003.

Babette Aicher, et al., Perifosine in Combination with Antimetabolites Induces Synergistic Effects on Cytotoxicity and Apoptosis in Human Colon, Multiple Myeloma, Breast, Renal, and Liver Tumor Cells, Abstract 203 (Poster) 22nd EORTC-NCI-AACR Symposium on Molecular Targets and Cancer Therapeutics, Nov. 17, 2010.

Babette Aicher, et al., Perifosine in Combination with Antimetabolites Induces Synergistic Effects on Cytotoxicity and Apoptosis in Human Colon, Multiple Myeloma, Breast, Renal, and Liver Tumor Cells, (Abstract) 22nd EORTC-NCI-AACR Symposium on Molecular Targets and Cancer Therapeutics, Nov. 17, 2010.

Johanna Bendell, et al., Randomized Phase II Study of Perifosine in Combination With Capecitabine (P-CAP) vs. Capecitabine Plus Placebo (CAP) in Patients With Second or Third Line Metastatic Colon Cancer (MCRC): Updated Results (Poster), 2010 Gastrointestinal Cancers Symposium, held Jan. 22-24, 2010, Orlando FL.

Johanna Bendell, et al., Randomized Phase II Study of Perifosine in Combination With Capecitabine (P-CAP) vs. Capecitabine Plus Placebo (CAP) in Patients With Second or Third Line Metastatic Colon Cancer (MCRC): Updated Results, (Abstract), 2010 Gastrointestinal Cancers Symposium, held Jan. 22-24, 2010, Orlando FL.

R. Birch, et al., Perifosine (KRX-0401)—An Active Agent in the Treatment of Patients with Advanced Sarcoma (Poster), 2007 ASCO Annual Meeting, held Jun. 1-5, 2007.

R. Birch, et al., Perifosine (P) as an active agent in the treatment of patients with advanced sarcoma, Journal of Clinical Oncology, 2007 ASCO Annual Meeting Proceedings Part I. vol. 25, No. 18S (Jun. 20 Supplement), 2007: 10059.

Rachel Midgley and David J Kerr, Capecitabine: have we got the dose right?, Nature Clinical Practice Oncology, pp. 17-24, Jan. 2009 vol. 6 No. 1.

D.C. Cho, et al. A phase II trial of perifosine in patients with advanced renal cell carcinoma (RCC) who have failed tyrosine kinase inhibitors (TKI), (Abstract), 2009 ASCO Annual Meeting, J Clin Oncol 27:15s, 2009 (suppl; abstr 5101).

D.C. Cho, et al. A phase II trial of perifosine in patients with advanced renal cell carcinoma (RCC) who have failed tyrosine kinase inhibitors (TKI), (Poster), 2009 ASCO Annual Meeting held May 29-Jun. 2, 2009, Orlando, Florida.

Daniel Cho, et al., Inhibition of Glycogen Synthase Kinase 3β (GSK3β) Enhances the In Vitro Activity of the Akt Inhibitor Perifosine in Renal Cell Carcinoma (RCC) Cell Lines (Poster), 98th AACR Annual Meeting—held Apr. 14-18, 2007; Los Angeles, CA.

Daniel Cho, et al., Inhibition of Glycogen Synthase Kinase 31β (GSK3β) Enhances the In Vitro Activity of the Akt Inhibitor Perifosine in Renal Cell Carcinoma (RCC) Cell Lines (Abstract No. 1823), 98th AACR Annual Meeting—held Apr. 14-18, 2007; Los Angeles, CA.

Diana Cirstea, M.D., et al., Combination of Nab-Rapamycin and Perifosine Induces Synergistic Cytotoxicity and Antitumor Activity Via Autophagy and Apoptosis in Multiple Myeloma (MM) (Poster), American Society of Hematology (ASH) 50th Annual Meeting and Exposition, held Dec. 6-9, 2008; San Francisco, California.

Diana Cirstea, M.D., et al., Combination of Nab-Rapamycin and Perifosine Induces Synergistic Cytotoxicity and Antitumor Activity Via Autophagy and Apoptosis in Multiple Myeloma (MM)

(Abstract), American Society of Hematology (ASH) 50th Annual Meeting and Exposition, held Dec. 6-9, 2008; San Francisco, California.

A. P. Conley, et al., A randomized phase II study of perifosine (P) plus imatinib for patients with imatinib-resistant gastrointestinal stromal tumor (GIST) (Abstract), 2009 ASCO Annual Meeting, J Clin Oncol 27:15s, 2009 (suppl; abstr 10563), held May 29 through Jun. 2, 2009, Orlando, FL.

A. P. Conley, et al., A randomized phase II study of perifosine (P) plus imatinib for patients with imatinib-resistant gastrointestinal stromal tumor (GIST) (Poster), 2009 ASCO Annual Meeting, held May 29-Jun. 2, 2009, Orlando, FL.

Irene M. Ghobrial, et al., Phase II Trial of the Novel Oral Akt Inhibitor Perifosine in Relapsed and/or Refractory Waldenström Macroglobulinemia (Poster), 2007 ASH Annual Meeting, held Dec. 8-11, 2007, Atlanta, GA.

Irene M. Ghobrial, et al., Phase II Trial of Perifosine (KRX-0401) in Relapsed and/or Refractory Waldenström Macroglobulinemia: Preliminary Results (Abstract), Blood (ASH Annual Meeting Abstracts), Nov. 2007; 110: 4493.

F. A. Greco, et al., Safety and pharmacokinetic (PK) study of perifosine plus capecitabine (PCAP) in patients (pts) with refractory metastatic colorectal cancer (mCRC), J Clin Oncol 28, 2010 (suppl; abstr e14086), 2010 ASCO Annual Meeting.

Bryan Hennessy, et al., Perifosine accumulates preferentially in tumor tissues: Correlation between accumulation in tumor tissue and inhibition of cell proliferation and tumor growth (Poster), AACR-NCI-EORTC International Conference: Molecular Targets and Cancer Therapeutics—held Oct. 22-26, 2007; San Francisco, CA.

Bryan Hennessy, et al., Perifosine accumulates preferentially in tumor tissues: Correlation between intratumoral accumulation and inhibition of cell proliferation and tumor growth (Abstract) AACR Meeting Abstracts, Oct. 2007; 2007: C178, AACR-NCI-EORTC International Conference: Molecular Targets and Cancer Therapeutics—held Oct. 22-26, 2007; San Francisco, CA.

Hoff P., et al., O-0017. Subset Analysis of 5-Fu Refractory Patients From a Randomized Ph II Study of Perifosine 1 Capecitabine (P-Cap) vs. Placebo 1 Capecitabine (Cap) In Patients With 2nd or 3rd Line Metastatic CRC (Abstract), 12th World Congress on Gastrointestinal Cancer, Barcelona, Spain, held Jun. 30-Jul. 2, 2010.

Paulo Hoff, et al., Subset Analysis of 5-Fu Refractory Patients From the Final Results of a Randomized Phase II Study of Perifosine in Combination With Capecitabine (P-Cap) vs. Placebo Plus Capecitabine (Cap) in Patients With Second or Third Line Metastatic Colorectal Cancer (mCRC) (Poster), 12th World Congress on Gastrointestinal Cancer, Barcelona, Spain, held Jun. 30-Jul. 2, 2010.

A. Huston, MD, et al., Combination of the Akt Inhibitor Perifosine with the Hsp90 Inhibitor 17-(dimethylaminoethylamino)-17-demethoxygeldanamycin (17-DMAG) has Synergistic Activity in Multiple Myeloma (Poster) 2005 ASH Annual Meeting, held Dec. 10-13, 2005; Atlanta, Georgia.

Alissa Huston, MD, et al., Combination of the AKT Inhibitor Perifosine with the HSP90 Inhibitor 17-(Dimethylaminoethylamino)-17-Demethoxygeldanamycin (17-DMAG) Has Synergistic Activity in Multiple Myeloma (MM) (Abstract) Blood (ASH Annual Meeting Abstracts) 2005 106: Abstract 1592.

A. Huston, MD, et al., The Role of the Akt Inhibitor Perifosine in Migration and Adhesion in Multiple Myeloma A (Poster) 2005 ASH Annual Meeting, held Dec. 10-13, 2005; Atlanta, Georgia.

Alissa Huston, MD, et al., The Role of the AKT Inhibitor Perifosine in Migration and Adhesion in Multiple Myeloma (MM) (Abstract) Blood (ASH Annual Meeting Abstracts) 2005 106: Abstract 2509.

A. Huston, MD, et al., Proteomic Analysis Identifies Differences in Multiple Myeloma Cells Sensitive and Resistant to Akt Inhibition (Poster) 2005 ASH Annual Meeting held Dec. 10-13, 2005; Atlanta, Georgia.

Alissa Huston, MD, et al., Proteomic Analysis Identifies Differences in Multiple Myeloma (MM) Cells Sensitive and Resistant to AKT Inhibition (Abstract) Blood (ASH Annual Meeting Abstracts) 2005 106: Abstract 3402.

Andrzej Jakubowiak, et al., A Multiple Myeloma Research Consortium (MMRC) Multicenter Phase I Trial of Perifosine (Krx-0401) in Combination With Lenalidomide and Dexamethasone in Patients With Relapsed or Refractory Multiple Myeloma (MM): Updated Results Introduction (Poster) 2008 Blood (ASH Annual Meeting Abstracts) 2008 112: Abstract 3691.

Hyo Song Kim, et al., Evaluation of Anticancer Drug Sensitivity and Gene Expression Patterns of a Novel Akt Inhibitor, Perifosine in Gastric Cancer (Poster) 2011 AACR Annual Meeting held Apr. 2-6, 2011.

Tae Soo Kim et al., Presentation Title: Antitumor activity of novel Akt inhibitor, perifosine in gastric cancer cell lines (Abstract No. 1965) 2011 AACR Annual Meeting held Apr. 2-6, 2011.

Andrew Lassman, et al., Clinical and Molecular-Metabolic Phase II Trial of Perifosine for Recurrent/Progressive Malignant Glioma (Abstract) $12^{th}$ Annual Meeting of the Society for Neurooncology held Nov. 15-18, 2007.

Ab Lassman, et al., Phase II Trial of Perifosine for Recurrent Malignant Glioma (Poster) $12^{th}$ Annual Meeting of the Society for Neurooncology held Nov. 15-18, 2007.

Zhijie Li, et al., Perifosine, as a single agent, inhibits neuroblastoma tumor cell growth in vitro and in vivo (Poster) 2009 AACR Annual Meeting held Apr. 18-22, 2009, Denver, CO.

Zhijie Li, et al, Perifosine, as a single agent, inhibits neuroblastoma tumor cell growth in in vitro and in vivo preclinical models (Abstract #3205) 2009 AACR Annual Meeting held Apr. 18-22, 2009, Denver, CO.

Zhijie Li, et al., Neuroblastoma tumors with different ALK mutations are sensitive to Perifosine (Poster) 101st Annual Meeting of the American Association for Cancer Research (AACR), Washington, DC. Apr. 21, 2010.

Zhijie Li, et al., Presentation Title: Neuroblastoma tumors with different ALK mutations are sensitive to Perifosine (Abstract No. 5248) 101st Annual Meeting of the American Association for Cancer Research (AACR), Washington, DC. Apr. 21, 2010.

Zhijie Li, et al., Perifosine, an Akt inhibitor, sensitizes Neuroblastoma to etoposide treatment (Poster) 2008.

Enrique Poradosu, et al., Perifosine selectively inhibits binding of Akt PH domain to PtdIns(3,4)P2 (Abstract #1645) 2007 AACR Annual Meeting held Apr. 14-18, 2007, Los Angeles, CA.

Enrique Poradosu, et al., Identification of Pharmacodynamic Markers for Effects of Perifosine (KRX0401) on the PI3K Pathway in vivo (Poster) 2005 AACR-NCI-EORTC International Conference on Molecular Targets and Cancer Therapeutics: Discovery, Biology, and Clinical Applications held Nov. 14-18, 2005.

Enrique Poradosu, et al., Identification of Pharmacodynamic Markers for Effects of Perifosine (KRX0401) on the PI3K Pathway in vivo (Abstract A194) 2005 AACR-NCI-EORTC International Conference on Molecular Targets and Cancer Therapeutics: Discovery, Biology, and Clinical Applications held Nov. 14-18, 2005.

Enrique Poradosu, Ph.D., Perifosine: An Akt Inhibitor in Clinical Trials, oral presentation at 2007 AACR Meeting.

Paul Richardson, MD, et al., Phase I/II of a Multicenter Trial of Perifosine (KRX-0401) + Bortezomib in Relapsed or Relapsed/Refractory Multiple Myeloma Patients Previously Relapsed From or Refractory to Bortezomib (Poster); Feb. 26, 2009.

Donald Richards, et al., Final Results of a Randomized Phase II Study of Perifosine in Combination With Capecitabine (P-CAP) vs. Placebo Plus Capecitabine (CAP) in Patients With Second or Third Line Metastatic Colorectal Cancer (mCRC) (Poster) 2010 ASCO Annual Meeting held Jun. 4-8, 2010—Chicago, IL; J Clin Oncol 28:15s, 2010 (suppl; abstr 3531).

Paul Richardson, MD, et al., Phase I/II Results of a Multicenter Trial of Perifosine (KRX-0401) + Bortezomib in Patients with Relapsed or Relapsed/Refractory Multiple Myeloma Who Were Previously Relapsed From or Refractory to Bortezomib; (Oral Session *Novel Therapies for Myeloma and Related Disorders*) Blood (ASH Annual Meeting Abstracts) 2008 112: Abstract 870.

Paul Richardson, MD, et al., A Multicenter Phase I/II Trial of Perifosine (Krx-0401) + Bortezomib in Relapsed or Relapsed/Refractory Multiple Myeloma Patients Previously Treated With Bortezomib: Phase I Results (Poster) Dec. 8, 2007 at the 49th Annual Meeting of the American Society of Hematology.

Paul Richardson, MD, et al., Phase I/II Report from a Multicenter Trial of Perifosine (KRX-0401) + Bortezomib in Patients with Relapsed or Relapsed/Refractory Multiple Myeloma Previously Treated with Bortezomib (Abstract) Blood (ASH Annual Meeting Abstracts) 2007 110: Abstract 1170.

Paul Richardson, MD, et al., A Phase I/II Study Evaluating the Safety and Efficacy of Perifosine + Bortezomib (+/− Dexamethasone) for Patients with Relapsed or Relapsed / Refractory Multiple Myeloma who were Previously Treated with Bortezomib (Power Point Presentation) 2008 ASH Meeting.

Paul Richardson, MD, et al., Perifosine in Combination with Bortezomib and Dexamethasone Extends Progression-Free Survival and Overall Survival in Relapsed/Refractory Multiple Myeloma Patients Previously Treated with Bortezombib: Updated Phase I/II Trial Results (Abstract No. 1869) (Poster Board 1-894) Blood (ASH Annual Meeting Abstracts) 2009, 114: Abstract 1869.

Paul Richardson, MD, et al.,Perifosine Plus Bortezomib and Dexamethasone Extends Progression-Free Survival and Overall Survival in Relapsed / Refractory Multiple Myeloma Patients Previously Treated With Bortezomib: Updated Results of the Phase I/II Trial (Poster), 2009 ASH Annual Meeting held Dec. 5-8, 2009, New Orleans.

PG Richardson, et al., Phase I/II Trial of Perifosine + Bortezomib in Rel/Ref MM Patients Previously Treated with Bortezomib (Abstract); Feb. 26, 2009.

Alexandros S. Ardavanis, et al., Salvage Treatment with Single-agent Capecitabine in Patients with Heavily Pretreated Advanced Colorectal Cancer, Anticancer Research 26: 1669-1672 (2006).

N. J. Vogelzang, et al., Phase II Study of Perifosine in Metastatic RCC (Clear and Non-Clear) Progressing After One Prior Therapy (Rx) With a VEGF Receptor Inhibitor (Abstract), 2009 ASCO Genitourinary Cancers Symposium held Feb. 26-28, 2009, Orlando, Florida.

Nicholas J. Vogelzang, et al., Phase II Study of Perifosine in Metastatic Renal Cell Carcinoma (Clear and Non-Clear) Progressing After One Prior Therapy (Rx) With a VEGF Receptor Inhibitor (Poster) 2009 ASCO Genitourinary Cancers Symposium held Feb. 26-28, 2009, Orlando, Florida.

N. J. Vogelzang, et al., Phase II Study of Perifosine in Metastatic Renal Cell Carcinoma (RCC) Progressing After Prior Therapy (RX) With a VEGF Receptor Inhibitor (Abstract) 2009 ASCO Annual Meeting, J Clin Oncol 27:15s, 2009 (suppl; abstr 5034).

Nicholas J. Vogelzang, et al., Phase II Study of Perifosine in Metastatic Renal Cell Carcinoma Progressing Either After One Prior Therapy (Rx) With A VEGF Receptor Inhibitor or a VEGF and an mTOr Inhibitor (Poster) 2009 ASCO Annual Meeting held May 29-Jun. 2, 2009, Orlando, Florida.

Ra Sasha Vukelja, et al., Randomized Phase II Study of Perifosine in Combination With Capecitabine vs. Capecitabine Alone in Patients With Second or Third Line Metastatic Colon Cancer (Poster) 2009 ASCO Annual Meeting held May 29-Jun. 2, 2009 in Orlando, Florida.

S. Vukelja, et al., Randomized phase II study of perifosine in combination with capecitabine versus capecitabine alone in patients with second- or third-line metastatic colon cancer, (Abstract No: 4081), 2009 ASCO Annual Meeting, J Clin Oncol 27:15s, 2009 (suppl; abstr 4081).

Apr. 2, 2012 Keryx Press Release.

Press release dated Apr. 8. 2010, New York by Keryx Biopharmaceuticals, Inc.

Press release dated Feb. 3, 2010, New York by Keryx Biopharmaceuticals, Inc.

Press release dated Jan. 21, 2010. New York by Keryx Biopharmaceuticals, Inc.

Press release dated Jan. 25. 2010. New York by Keryx Biopharmaceuticals, Inc.

Press release dated Jun. 1, 2010, New York by Keryx Biopharmaceuticals. Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Oct. 17, 2011 (ongoing). sponsored by Keryx/AOI Pharmaceuticals, Inc.

"A Phase III Randomized Study to Assess the Efficacy and Safety of Perifosine Plus Capecitabine Versus Placebo II Plus Capecitabine in Patients With Refractory Advanced Colorectal Cancer" recorded in ClinicalTrials.gov registry, ClinicalTrials Identifier: NCT01097018, data updated Oct. 16, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jul. 26, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicaiTrials.gov registry, ClinicalTrials Identifier: NCT01097018, data updated Jul. 19, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated May 20, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicaiTrials.gov registry, ClinicalTrials Identifier: NCT01097018, data updated Apr. 18, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Mar. 7, 2011 (ongoing), sponsored by Keryx/AOI Pharmaceuticals, Inc.

"Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Feb. 17, 2011 (ongoing). sponsored by Keryx/AOI Pharmaceuticals, Inc.

"A Phase II Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry. ClinicalTrials Identifier: NCT01097018, data updated Jan. 11, 2011 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Dec. 15, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Nov. 22, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Nov. 4, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Oct. 19, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Sep. 28, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Aug. 27, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Aug. 4, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jul. 16, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jun. 28, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Jun. 2, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated May 19, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 27, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 12, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 7, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 2, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Apr. 1, 2010 (ongoing), sponsored by Keryx/AOI Pharmaceuticals, Inc.

"A Phase III Randomized Study to Assess the Efficacy and Safety of Perifosine Plus Capecitabine Versus Placebo Plus Capecitabine in Patients With Refractory Advanced Colorectal Cancer" recorded in ClinicalTrials.gov registry, ClinicalTrials Identifier: NCT01097018, data updated Mar. 31, 2010 (ongoing), sponsored by Keryx/AOI Pharmaceuticals, Inc.

"A Randomized Placebo—Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Nov. 10, 2011, sponsored By Keryx/AOI Pharmaceuticals, Inc.

"A Randomized Placebo—Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated May 9, 2011, sponsored by Keryx/AOI Pharmaceuticals, Inc.

"A Randomized Placebo—Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Oct. 17, 2011, sponsored by Keryx/AOI Pharmaceuticals, Inc.

"A Randomized Placebo—Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Sep. 22, 2009, sponsored By Keryx/AOI Pharmaceuticals, Inc.

"A Randomized Placebo—Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Feb. 16, 2009, sponsored By Keryx/AOI Pharmaceuticals, Inc.

"A Randomized Placebo—Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Apr. 7, 2008, sponsored by Keryx/AOI Pharmaceuticals, Inc.

"A Randomized Placebo—Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Oct. 16, 2007, sponsored by Keryx/AOI Pharmaceuticals, Inc.

"A Randomized Placebo—Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Mar. 15, 2007, sponsored by Keryx/AOI Pharmaceuticals, Inc.

"A Randomized Placebo—Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Feb. 1, 2007, sponsored by Keryx/AOI Pharmaceuticals, Inc.

"A Randomized Placebo—Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Jan. 31, 2007, sponsored by Keryx/AOI Pharmaceuticals, Inc.

"A Randomized Placebo—Controlled Study of Perifosine in Combination With Single Agent Chemotherapy for Metastatic Cancer Patients" (Phase II Study) recorded in ClinicalTrials.gov registry, ClinicalTrials Identifier: NCT00398879, data updated Nov. 13, 2006, sponsored by Keryx/AOI Pharmaceuticals, Inc.

"A Phase I Study of Perifosine + Capecitabine for Patients With Advanced Colon Cancer" recorded in ClinicalTrials.gov registry, ClinicalTrials Identifier: NCT01048580, dated Nov. 14, 2011.

"A Phase I Study of Perifosine + Capecitabine for Patients With Advanced Colon Cancer" recorded in ClinicalTrials.gov registry, ClinicalTrials Identifier: NCT01048580, dated Oct. 17, 2011.

"A Phase I Study of Perifosine + Capecitabine for Patients With Advanced Colon Cancer" recorded in ClinicalTrials.gov registry, ClinicalTrials Identifier: NCT01048580, dated Jul. 19, 2011.

"A Phase I Study of Perifosine + Capecitabine for Patients With Advanced Colon Cancer" recorded in ClinicalTrials.gov registry, ClinicalTrials Identifier: NCT01048580, dated Mar. 31, 2010.

"A Phase I Study of Perifosine + Capecitabine for Patients With Advanced Colon Cancer" recorded in ClinicalTrials.gov registry, ClinicalTrials Identifier: NCT01048580, dated Jan. 13, 2010.

"A Phase I Study of Perifosine + Capecitabine for Patients With Advanced Colon Cancer" recorded in ClinicalTrials.gov registry, ClinicalTrials Identifier: NCT01048580, dated Jan. 12, 2010.

Argiris et al., A phase II trial ofperifosine, an oral alkyiphospholipid, in recurrent or metastatic head and neck cancer. Cancer Bioi Ther. Jul. 2006;5( 7): 766-70.

A Wada et al., An EORTC-IDBBC phase I study of gemcitabine and continuous infusion 5-fluorouracil in patients with metastatic breast cancer resistant to anthracyclines or pre-treated with both anthracyclines and taxanes. Eur J Cancer. Apr. 2002;38(6):773-8.

Banker and Rhodes (Eds.), *Modern Pharmaceutics*. 3rd Edition, Revised and Expanded. pp. 451 & 596, Marcel Dekker Inc., ( 1996).

Ghobrial et al. Emerging Drugs in multiple myeloma. Expert Opin. Emerg. Drugs. Mar. 2007; 12(1): 155-63. (Author Proof Copy).

Goodman & Gillman. *The Pharmacological Basis of Therapeutic*. 9'" Edit pp. 1225-1232 ( 1996).

Hennessy et al., Pharmacod)namic markers of perifosine efficacy. Clin Cancer Res. Dec. 15, 2007; 13(24 ):7421-31.

International Search Report for PCT application No. PCT/US2006/002988 (or PCT publication No. WO 2006/081452) dated Nov. 22, 2007.

International Search Report for PCT application No. PCT/US2011/030800 (or PCT publication No. WO 20111123691) dated Jul. 25, 2011.

Knebel et al.. Quantification ofperifosine. An alkylphosphocholine anti-tumour agent. in plasma by pneumatically assisted electrospray tandem mass spectrometry coupled with high-performance liquid chromatography. $J_1$Chromatogr B Biomed Sci Appl. Jan. 22, 1999:721(2):257-69.

Posadas et al., A phase II study of perifosine in androgen independent prostate cancer. Cancer Biol Ther. Oct. 2005:4(10):1133-7.

Press release dated May 31. 2009, New York by Keryx Biopharmaceuticals. Inc.

Ruiter et al. Submicromolar doses of alkylphospholipids induce rapid internalization, but not activation, of epidermal growth factor receptor and concomitant MAPK?ERK activation in A431 cells. Int. J. Cancer. Dec. 1, 2002; 102(4):343-50.

Wolff M.E. (Ed.) "*Burger ●s .Medicinal Chemistry .And Drug Discovery*" 5'thEdition, vol. I: Principles and Practice. pp. 975-977, John Wile & Sons. Inc. ( 1995).

Written Opinion for PCT application No. PCT/US2006/002988 (or PCT publication No. WO 2006:081452) , dated Sep. 25, 2007.

Written Opinion for PCT application No. PCT/US2011/030800 (or PCT publication No. WO 2011/123691), dated Jul. 25, 2011.

Bendell et al., "Randomized Placebo—Controlled Phase II Trial of Perifosine Plus Capecitabine as Second- or Third-Line Therapy in Patients With Metastatic Colorectal Cancer," *J. Clin. Oneal.* (2011 ), http://jco.ascopubs.org/cgi/doi/1 0.1200/JC0.20 11.36.1980, 8 pages.

Richardson et al, "Perifosine Plus Bortezomib and Dexamethasone in Patients with Relapsed/Refractory Multiple Myeloma Previously Treated with Bortezomib: Results of a Multicenter Phase 1/11 Trial," *J. Clin. Oneal.* (2011 ), http://jco.ascopubs.org/cgi/doi/1 0.1200/JC0. 201 0.33.9788, 11 pages.

\* cited by examiner

USE OF PERIFOSINE IN COMBINATION WITH ANTIMETABOLITES FOR THE TREATMENT OF BENIGN AND MALIGNANT ONCOSES IN HUMANS AND MAMMALS

CROSS-REFERENCE TO RELATED APPLICATIONS

This application is a continuation of U.S. patent application Ser. No. 10/632,187, filed on Jul. 30, 2003 now U.S. Pat. No. 8,389,497, which claims the benefit of U.S. Provisional Application No. 60/399,615, filed Jul. 30, 2002, which is hereby incorporated by reference.

BACKGROUND OF THE INVENTION

Alkylphosphocholines are a new class of organic compounds, which exhibit diversified anti-neoplastic activities (M. Lohmeyer and R. Bittman, Antitumor Ether Lipids and Alkylphosphocholines, DOF, 19 (11), 1021-103 7 (1994)). The effect of the alkylphosphocholines in this connection may be based on different, molecular and biochemical mechanisms, some of which take place on the level of the plasma membrane of the cell.

It is well known that alkylphosphocholines influence inositol metabolism, the interaction with phospholipases or inhibition of protein kinase C and thus that this class of substances has a general influence on cellular signal transduction (K. Maly et al., Interference of New Alkylphospholipid Analogues With Mitogenic Signal Transduction, Anti-Cancer Drug Design, 10, 411-425 (1995); and P. Hilgard, et al., D21266, A New Heterocyclic Alkylphospholipid with Antitumor Activity, Eur. J. Cancer, 33 (3), 442-446 (1997)). Thus, the alkylphosphocholine perifosine shows growth-inhibitory properties in relation to various melanoma, CNS, lung, colon, prostate and breast cancer cell lines with an $IC_{50}$ ranging from 0.2 to 20 μM.

It is further known that perifosine blocks tumor cells in the $G_1$-S and G2-M phase of the cell cycle (V. Patel, et al., A Novel Alkylphospholipid, Induces p. 21 $^{Waf1}$ Expression in Squamous Carcinoma Cells through a p53-independent Pathway, Leading to Loss in Cyclin dependent Kinase Activity and Cell Cycle Arrest, Cancer Research 62, 1401-1409 (2002)).

It is known that the use of alkylphosphocholines before or together with radiation therapy leads its synergistic effects during the treatment of tumors (P. Principe et al., Evaluation of Combinations of Antineoplastic Ether Phospholipids and Chemotherapeutic Drugs, Anti-Cancer Drugs, 3 (6), 577-587 (1992)). It has also been reported that different glycerol-3-phospholipids, such as ET-18-OOCH$_3$, in combination with different DNA-interacting substances or tubulin binders increase the anti-tumor activity in vitro in a different tumor cell lines (P. Principe et al., Synergistic Cytotoxic Effect of Aza-alkylphospholipids in Association with Chemotherapeutic Drugs, J. Lipid Mediators Cell Signalling, 10 (1-2), 171-173(1994)).

BRIEF SUMMARY OF THE INVENTION

Surprisingly, it was now possible to show that linear alkylphosphocholines of the general Formulas I and II are suitable for use in a combination according to the invention with other drug products for the treatment of benign and malignant oncoses in humans and mammals.

In this connection, the present invention relates to the novel use of alkylphosphocholine in combination with antitumor medications for art-recognized therapeutic activities attributed to the treatment of benign and malignant oncoses in humans and mammals.

It is therefore an object of this invention to provide a novel means of treating tumors with an inventive combination of linear alkylphosphocholines and anti-tumor substances.

DETAILED DESCRIPTION OF THE INVENTION

The present invention provides a novel use of linear alkylphosphocholines of the general Formulas I and II in an inventive combination with other medicinal drugs for the treatment of benign and malignant oncoses in humans and mammals. According to one aspect of the invention, the compounds of the general Formulas I and II can be used in an inventive combination with anti-tumor substances. Anti-tumor substances may be alkylating agents, anti-metabolites, plant alkaloids, platinum compounds, tumor antibiotics and agonists or antagonists of natural hormones. The anti-tumor substances may be selected from, but are not restricted to cis-platinum, carboplatinum, oxaliplatinum, bleomycin, doxorubicin, methotrexate, paclitaxel, docetaxel, vincristine, vinblastine, etoposide, teniposide, ifosfamide, cyclophosphamide, 5-fluorouracil, fludarabin, gemcitabine and cytarabine.

It is moreover possible for the alkylphosphocholines of the general Formula I and II to be employed in a claimed combination with inhibitors of signal transduction in the form of high and low molecular weight inhibitors of receptor and/or cytosolic kinases. These inhibitors may be selected from but not restricted to monoclonal antibodies and heterocyclic compounds.

The alkylphosphocholines of the general Formulas I and II, on which the invention is based, may be used in the form of finished medicinal drugs.

The compounds, on which the invention is based, are described by the general Formulas I and II:

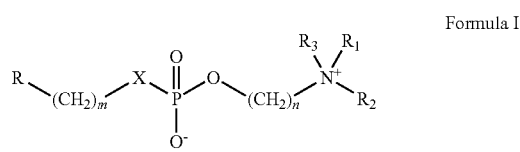

Formula I

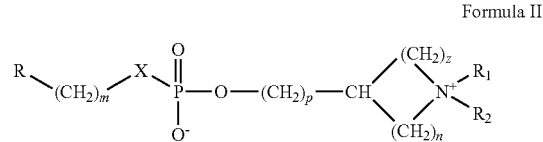

Formula II in which, independently of one another, n, m, p, z is a whole number between 0 and 4, is O, S, NH;

R is hydrogen, a linear or branched $C_1$ to $C_{20}$ alkyl group, which may be saturated or unsaturated with one to three double and/or triple bonds and unsubstituted or optionally substituted at the same or at different carbon atoms with one, two or more halogen, nitro, cyano, hydroxy, $C_1$ to $C_6$ alkoxy, amino, mono-($C_1$ to $C_4$) alkylamino or di-($C_1$ to $C_4$) alkylamino groups, $R_1$, $R_2$, $R_3$ independently of one another represent hydrogen, a linear or branched ($C_1$ to $C_6$) alkyl group, preferably methyl and ethyl, a ($C_3$ to CO cyclo alkyl group, which may be unsubstituted or optionally substituted at the same or different carbon atoms with one, two or more halogen, nitro, cyano, hydroxy, $C_1$ to $C_6$ alkoxy, amino, mono-($C_1$ to $C_4$) alkylamino or di-($C_1$ to $C_4$) alkylamino groups.

According to a further aspect of the invention, a method for controlling tumors in humans and in mammals is provided and comprises administering at least one of the compounds of the general Formula I and II on which the invention is based to the human or a mammal in an amount effective for tumor treatment before or during a treatment with approved antitumor substances.

The therapeutically effective dose, to be administered for the treatment, of the particular compound of the general formula I and II on which the invention is based depends inter alia on the nature and the stage of the oncosis, the age and sex of the patient, the mode of administration and the duration of treatment.

The compounds on which the invention are based can be administered in a drug product as liquid, semisolid and solid drug forms. This takes place in the manner suitable in each case in the form of aerosols, oral powders, dusting powders and epipastics, uncoated tablets, coated tablets, emulsions, foams, solutions, suspensions, gels, ointments, pastes, pills, pastilles, capsules or suppositories.

EXAMPLES

Example 1

Administration of Perifosine (D-21266) in Combination with Cisplatin

In vivo Experiment: DMBA-induced rat mammary carcinoma model
Experimental Animal: Sprague-Dawley rat, female
Procedure: The mammary carcinoma was induced by a single oral dose of DMBA. The animals received perifosine from day 0 to day 14 and were observed up to day 42. The weight of the tumor mass was estimated by palpation and comparison with plastic models. The initial weight is set equal to 100%.
Administration: Perifosin 14×6.81 mg/kg p.o.
   Cis-platinum 4×1 mg/kg i.p.
Effect: Reduction in the tumor was distinctly greater and longer through the combination treatment than through the single treatment in each case.

TABLE 1

| Treatment | Tumor Starting Weight (g) | Day 21, Change in % | p Test vs. Control |
| --- | --- | --- | --- |
| Control | 1.0 | 875 | — |
| Perifosin (D-21266) | 0.9 | −25 | <0.001 |
| Cis-platinum | 0.9 | 410 | 0.120 |
| Perifosin (D-21266) + Cis-platinum | 0.8 | −75 | <0.001 |

Example 2

Administration of Perifosine in Combination with Cyclophosphamide

In vivo Experiment: DMBA-induced rat mammary carcinoma model
Experimental Animal: Sprague-Dawley rat, female
Procedure: The mammary carcinoma was induced by a single oral dose of DMBA. The animals received perifosine from day 0 to day 14 and were observed up to day 42. The weight of the tumor mass was estimated by palpation and comparison with plastic models. The initial weight is set equal to 100%.
Administration: Perifosine 14×6.81 mg/kg p.o.
   Cyclophosphamide 100 mg/kg, VZ 0, i.v.
Effect: Reduction in the tumor was distinctly greater and longer through the combination treatment than through the single treatment in each case.

TABLE 2

| Treatment | Tumor Starting Weight (g) | Day 21, Change in % | p Test vs. Control |
| --- | --- | --- | --- |
| Control | 1.0 | 875 | — |
| Perifosin (D-21266) | 0.9 | −25 | <0.001 |
| Cyclophosphamide | 0.9 | 500 | 0.011 |
| Perifosin (D-21266) + Cyclophosphamide | 0.8 | −83.3 | <0.001 |

Example 3

Administration of Perifosine in Combination with Adriamycin

In vivo Experiment: DMBA-induced rat mammary carcinoma model
Experimental Animal: Sprague-Dawley rat, female
Procedure: The mammary carcinoma was induced by a single oral dose of DMBA. The animals received perifosine from day 0 to day 14 and were observed up to day 42. The eight of the tumor was mass was estimated by palpation and comparison with plastic models. The initial weight is set equal to 100%.
Administration: Perifosine 14×6.81 mg/kg p.o.
   Adriamycin 4×2.15 mg/kg i.p.
Effect: Reduction in the tumor was distinctly greater and longer through the combination treatment than through the single treatment in each case.

TABLE 3

| Treatment | Tumor Starting Weight (g) | Day 21, Change in % | p Test vs. Control |
| --- | --- | --- | --- |
| Control | 1.0 | 875 | — |
| Perifosin (D-21266) | 0.9 | −25 | <0.001 |
| Adriamycin | 1.0 | 781 | 0.197 |
| Perifosin (D-21266) + Adriamycin | 1.9 | −70 | <0.001 |

In the manner described above, the present invention thus provides a method for the use of alkylphosphocholines in combination with antitumor medications for the treatment of benign and malignant oncoses in humans and mammals. While this invention has been described with reference to the preferred embodiments, these are illustrative only and not limiting, having been presented by way of example. Other modifications will become apparent to those skilled in the art by study of the specification and drawings. It is thus intended that the following appended claims include such modifications as fall within the spirit and scope of the present invention.

What we claim is:
1. A method for treating a benign or malignant oncosis, comprising administering to a human subject in need thereof a therapeutically effective amount of octadecyl 1,1-dimeth- ylpiperidinium-4-yl phosphate (perifosine), wherein the perifosine is administered before and/or during treatment with at least one antimetabolite.

2. The method of claim 1, wherein the perifosine is administered before treatment with at least one antimetabolite.

3. The method of claim 1, wherein the perifosine is administered during treatment with at least one antimetabolite.

4. The method of claim 1, wherein the antimetabolite is 5-fluorouracil.

5. The method of claim 1, wherein the antimetabolite is cytarabine.

6. The method of claim 1, wherein the antimetabolite is gemcitabine.

7. The method of claim 1, wherein the oncosis is a breast, lung, prostate, melanoma or colon oncosis.

8. The method of claim 1, wherein the perifosine is orally administered.

9. The method of claim 1, wherein the perifosine is administered as a tablet, pill or capsule.

10. A method for treating a malignant oncosis, comprising administering to a human subject in need thereof a therapeutically effective amount of perifosine, wherein the perifosine is administered before and/or during treatment with at least one antimetabolite.

11. The method of claim 10, wherein the perifosine is administered before treatment with at least one antimetabolite.

12. The method of claim 10, wherein the perifosine is administered during treatment with at least one antimetabolite.

13. The method of claim 10, wherein the antimetabolite is 5-fluorouracil.

14. The method of claim 10, wherein the antimetabolite is cytarabine.

15. The method of claim 10, wherein the antimetabolite is gemcitabine.

16. The method of claim 10, wherein the oncosis is a breast, lung, prostate, melanoma or colon oncosis.

17. The method of claim 10, wherein the oncosis is a colon oncosis.

18. The method of claim 10, wherein the perifosine is orally administered.

19. The method of claim 10, wherein the perifosine is administered as a tablet, pill or capsule.

* * * * *

UNITED STATES PATENT AND TRADEMARK OFFICE
CERTIFICATE OF CORRECTION

| | | |
|---|---|---|
| PATENT NO. | : 8,551,977 B2 | Page 1 of 1 |
| APPLICATION NO. | : 12/751454 | |
| DATED | : October 8, 2013 | |
| INVENTOR(S) | : Jürgen Engel et al. | |

It is certified that error appears in the above-identified patent and that said Letters Patent is hereby corrected as shown below:

On the Title Page, for item 75:

"Jurgen" should read "Jürgen"

and

"Gunther" should read "Günther"

Signed and Sealed this
Eleventh Day of February, 2014

Michelle K. Lee
*Deputy Director of the United States Patent and Trademark Office*